US00PP35764P2

(12) United States Plant Patent
Zlesak

(10) Patent No.: US PP35,764 P2
(45) Date of Patent: Apr. 23, 2024

(54) ***PHYSOCARPUS* PLANT NAMED 'SUECKAT'**

(50) Latin Name: *Physocarpus opulifolius*
Varietal Denomination: SueCKat

(71) Applicant: David Charles Zlesak, River Falls, WI (US)

(72) Inventor: David Charles Zlesak, River Falls, WI (US)

( * ) Notice: Subject to any disclaimer, the term of this patent is extended or adjusted under 35 U.S.C. 154(b) by 0 days.

(21) Appl. No.: 18/445,471

(22) Filed: Sep. 5, 2023

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./226
See application file for complete search history.

*Primary Examiner* — Susan McCormick Ewoldt

(57) ABSTRACT

'SueCKat' is a new and distinct cultivar of *Physocarpus opulifolius* plant having an upright, mounded, dense plant habit; compact overall plant size; strong branching characteristics; small yellow-green foliage; short internode length that becomes shorter as the growing season progresses; resistance to powdery mildew; corymbs of small white flowers; green follicle color with very light coral-pink highlights in full sun for about a month after fertilization; and ability to root and grow vigorously from softwood and semi-hardwood stem cuttings.

9 Drawing Sheets

Latin name of genus and species: *Physocarpus opulifolius.*

Variety denomination: 'SueCKat'.

BACKGROUND OF THE INVENTION

The present invention relates to a new and distinct cultivar of *Physocarpus opulifolius* and will be referred to hereafter by its cultivar name, 'SueCKat'. *Physocarpus opulifolius* (commonly known as ninebark, common ninebark, Altantic ninebark, and Eastern ninebark) is a deciduous shrub grown primarily for landscape use. The key objective within the *Physocarpus opulifolius* breeding program I initiated in St. Paul, Minn. in 2001 and now continue in River Falls, Wisc. is to develop new *Physocarpus opulifolius* cultivars that are compact growing, well-branched, healthy, and possess colorful foliage.

'SueCKat' originated as a unique seedling within what can be described as an $F_2$ population. Open-pollinated seed was collected off of 'ZLEBic5' (disclosed in U.S. Plant Pat. No. 31,235) to develop the population from which 'SueCKat' was selected. 'ZLEBic5' is cross of *Physocarpus opulifolius* 'Donna May' (disclosed in U.S. Plant Pat. No. 22,634) as the female parent and *Physocarpus opulifolius* 'Dart's Gold' (not patented) as the male parent. 'ZLEBic5' (maternal parent of 'SueCKat') was growing in isolation with eleven of its full siblings. Ninebark displays self-incompatibility, and it is expected that the developing seeds on 'ZLEBic5' were from crosses between 'ZLEBic5' and genetically compatible full siblings. The pollination that led to the population of seedlings from which 'SueCKat' was identified occurred in spring 2016. The seeds of this population germinated during the winter of 2016/2017 indoors under florescent lights in River Falls, Wisc. During the first growing season, seedlings with attractive foliage color, relatively compact growth habit, and powdery mildew resistance were retained and in August 2017 planted in an outdoor ground bed in River Falls, Wisc. 'SueCKat' stood out as a highly desirable genotype among this seedling population as it matured, in part due to it having yellow-green foliage and a dense, tight, and uniform plant habit. 'SueCKat' was first asexually propagated using semi-hardwood and softwood stem cuttings during the summer of 2019 in River Falls, Wisc. I have found that the characteristics of 'SueCKat' are stable and true to type over successive generations of vegetative propagation.

'SueCKat' is unique relative to other ninebark seedlings in my breeding program and all cultivars I am aware of because of especially its ability, to have reduced internode length on new growth from mid-summer into fall. Decreasing internode length over the growing season leads to shorter stems with a denser foliage display around the plant perimeter and stems that are able to hold themselves up better without arching or sagging as much as other ninebark cultivars. Additionally, 'SueCKat' has relatively little anthocyanin pigment (pigment leads to pink to red color) in its flowers, fruits, and stems. This leads to a unique look to the plant with it having minimal pink highlights in the flowers, fruits, and stems.

SUMMARY OF THE INVENTION

The primary objective of the breeding goal was substantially achieved, along with other desirable improvements, as evidenced by the following unique combination of characteristics that are outstanding in the new variety and that distinguish it from other ninebark in my breeding program, as well as from all other cultivars of *Physocarpus opulifolius* of which I am aware:

1. Upright, mounded, dense plant habit;
2. Compact overall plant size;
3. Strong branching characteristics;
4. Small yellow-green foliage;
5. Short internode length that becomes shorter as the growing season progresses;
6. Resistance to powdery mildew;

7. Corymbs of small white flowers;
8. Green follicle color with very light coral-pink highlights in full sun for about a month after fertilization;
9. Ability to root and grow vigorously from softwood and semi-hardwood stem cuttings.

Asexual reproduction of this new cultivar by rooting of softwood and semi-hardwood cuttings, as performed at River Falls, Wisc., shows that the foregoing and all other characteristics and distinctions come true to form and are established and transmitted through successive generations of asexual propagation.

COMPARISON WITH PARENTS

'SueCKat' is a seedling of 'ZLEBic5' (maternal parent) most likely crossed with a nearby growing full sibling of 'ZLEBic5' ('ZLEBic5' and its full siblings are hybrids of 'Donna May' as the female parent and 'Dart's Gold' as the male parent). 'SueCKat' is similar to 'ZLEBic5' in that both have relatively small leaves, branch freely on current season's stems without pruning, and have a relatively similar mature plant size ('SueCKat' is slightly larger than 'ZLEBic5'). 'SueCKat' differs from 'ZLEBic5' in that it has yellow-green foliage and 'ZLEBic5' has primarily purple foliage. 'ZLEBic5' reblooms reliably later in summer, while 'SueCKat' typically only blooms in spring. 'SueCKat' is different from the eleven full siblings of 'ZLEBic5' that were growing adjacent to 'ZLEBic5' and one is most likely its paternal parent. None of the eleven full siblings of 'ZLEBic5' or 'ZLEBic5' display a routine decrease in internode length on current season stems as the growing season progresses.

COMPARISON OF 'SUECKAT' WITH SIMILAR CULTIVARS

The *Physocarpus opulifolius* cultivar with the greatest similarity to 'SueCKat' is *Physocarpus opulifolius* 'ZLEMichael' (disclosed in U.S. Plant Pat. No. 34,243). Foliage color, branching habit, compact growth, and overall plant size are similar between these cultivars. Differences are that the leaves of 'SueCKat' are smaller than 'ZLEMichael' and the internode length of 'SueCKat' becomes shorter as the season progresses while the internode length of 'ZLEMichael' stays relatively consistent over the growing season. Additionally, both cultivars have minimal anthocyanin pigment (observed as pink color) in the stems, flowers, and developing follicles compared to other ninebark cultivars. 'SueCKat' has less pink coloration in the stems, flowers, and, developing follicles than 'ZLEMichael'.

BRIEF DESCRIPTION OF THE DRAWINGS

The accompanying colored photographs illustrate key features of 'SueCKat'. Photographs show the colors as true as it is reasonably possible to obtain with colored reproductions of this type. Colors in the photographs may differ slightly from the color values cited in the detailed botanical description, which accurately describe the colors of 'SueCKat'. The plant of 'SueCKat' photographed is the ortet growing in a garden bed in River Falls, Wisc.

DETAILED BOTANICAL DESCRIPTION

Figure 1:
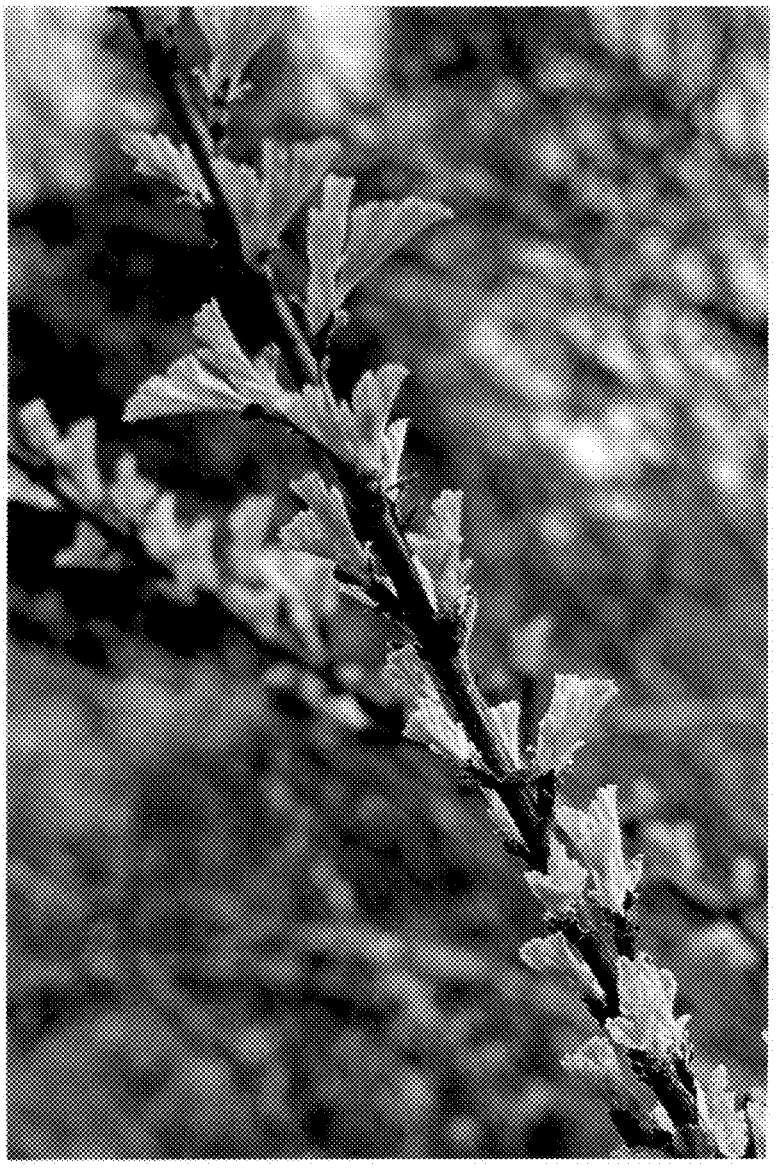
FIG. 1 illustrates emerging foliage in April.
Figure 2:
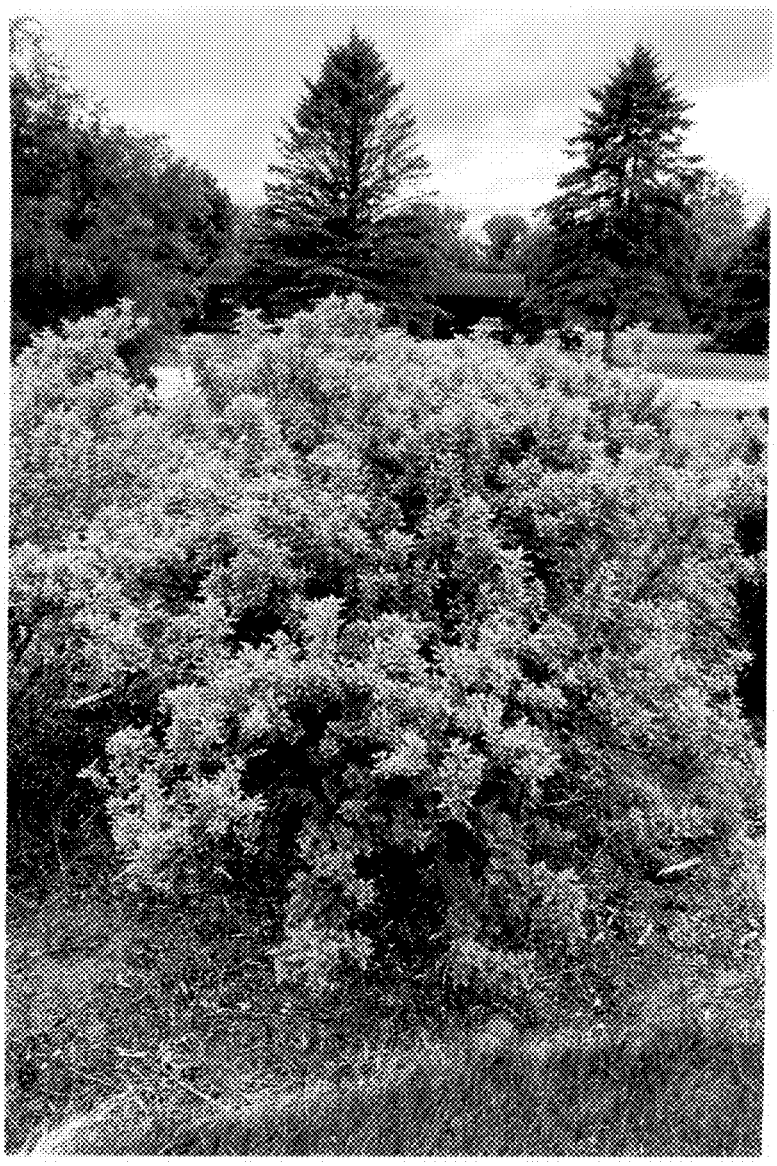
FIG. 2 illustrates expanding foliage in early May.
Figure 3:
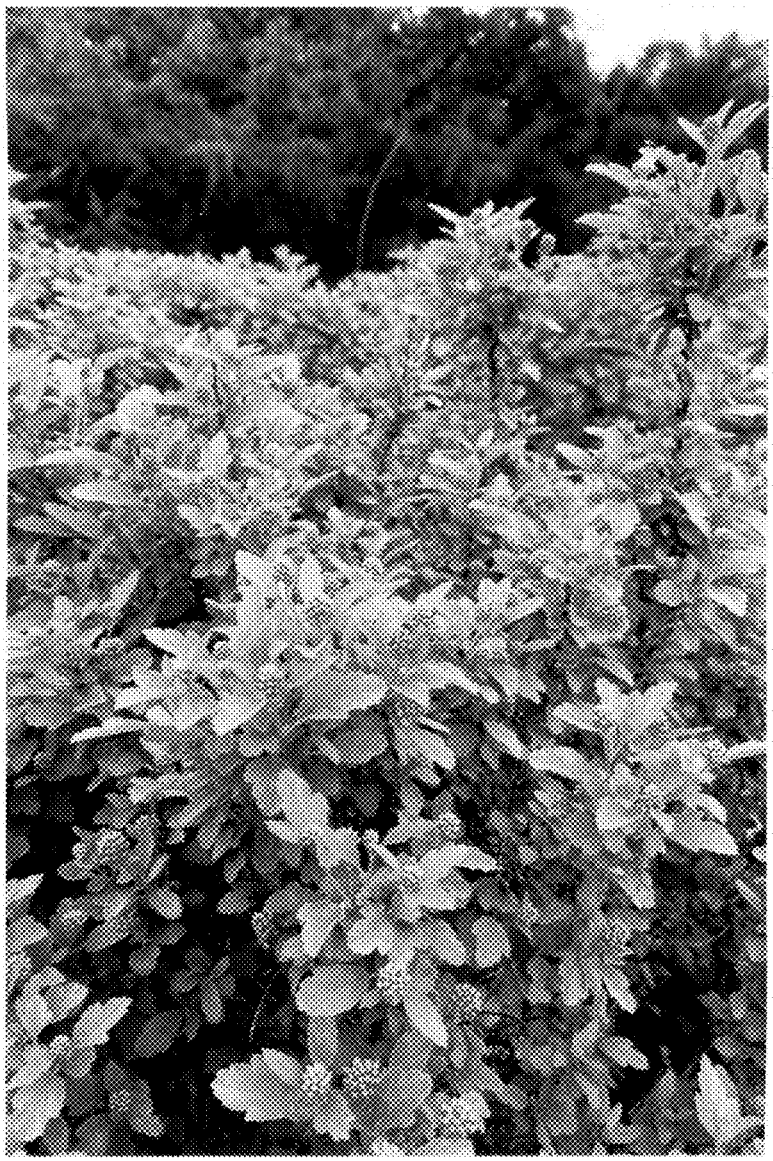
FIG. 3 illustrates developing inflorescences in mid May.
Figure 4:
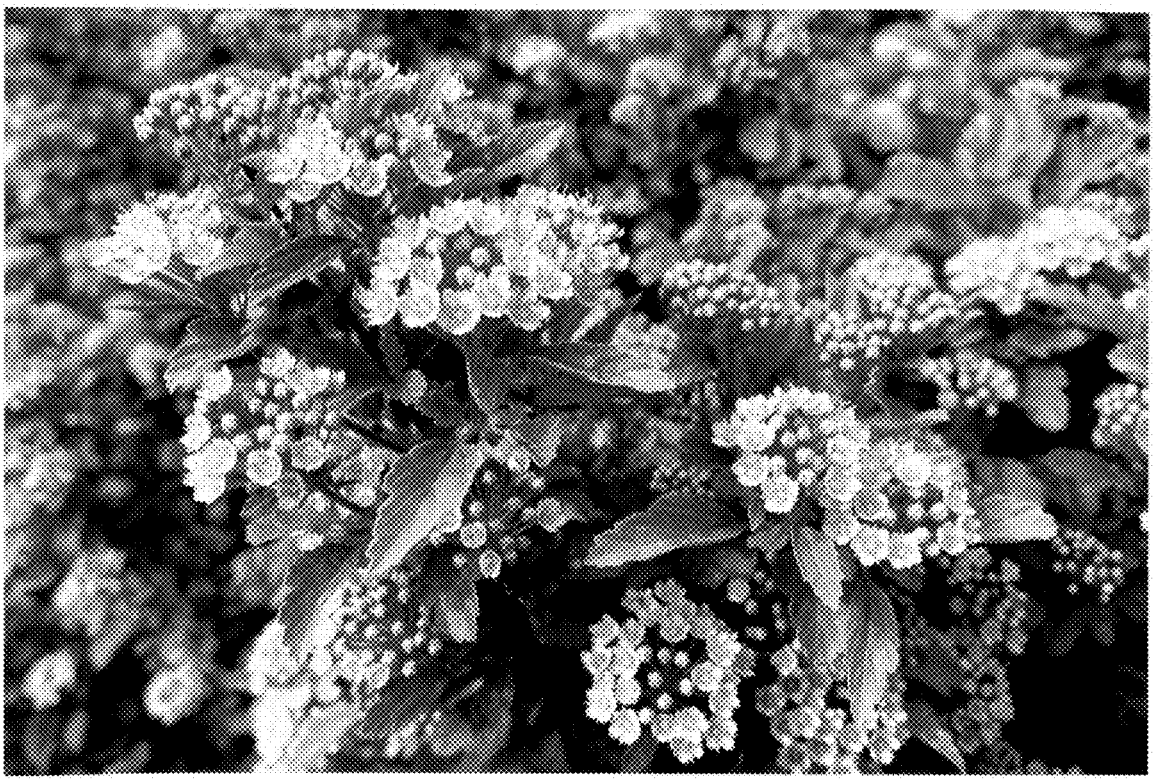
FIG. 4 illustrates dense floral coverage in early June.
Figure 5:
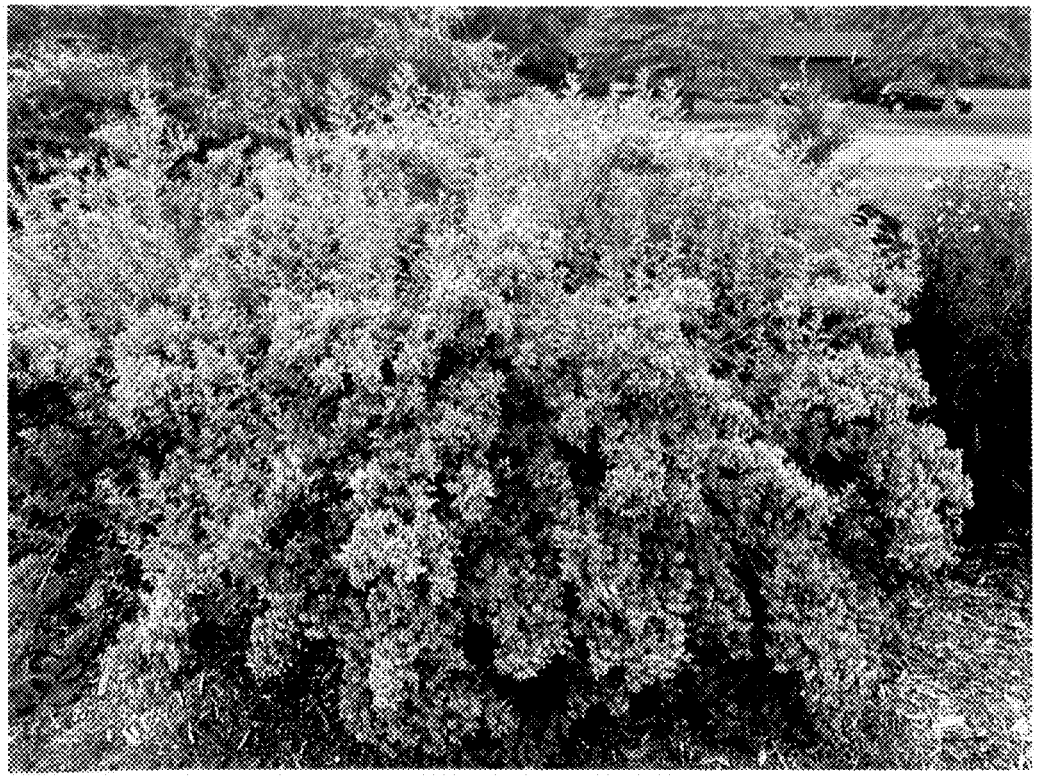
FIG. 5 illustrates the overall plant in late June after it blooms.
Figure 6:
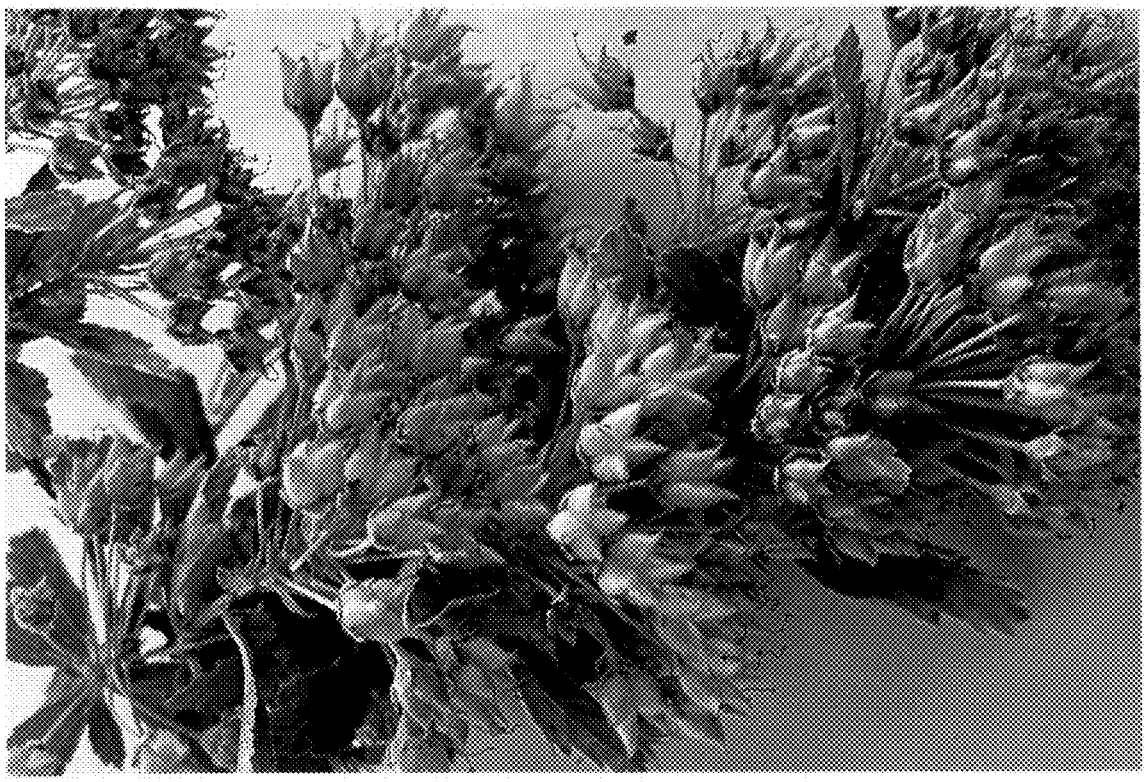
FIG. 6 illustrates developing fruit in late June.
Figure 7:
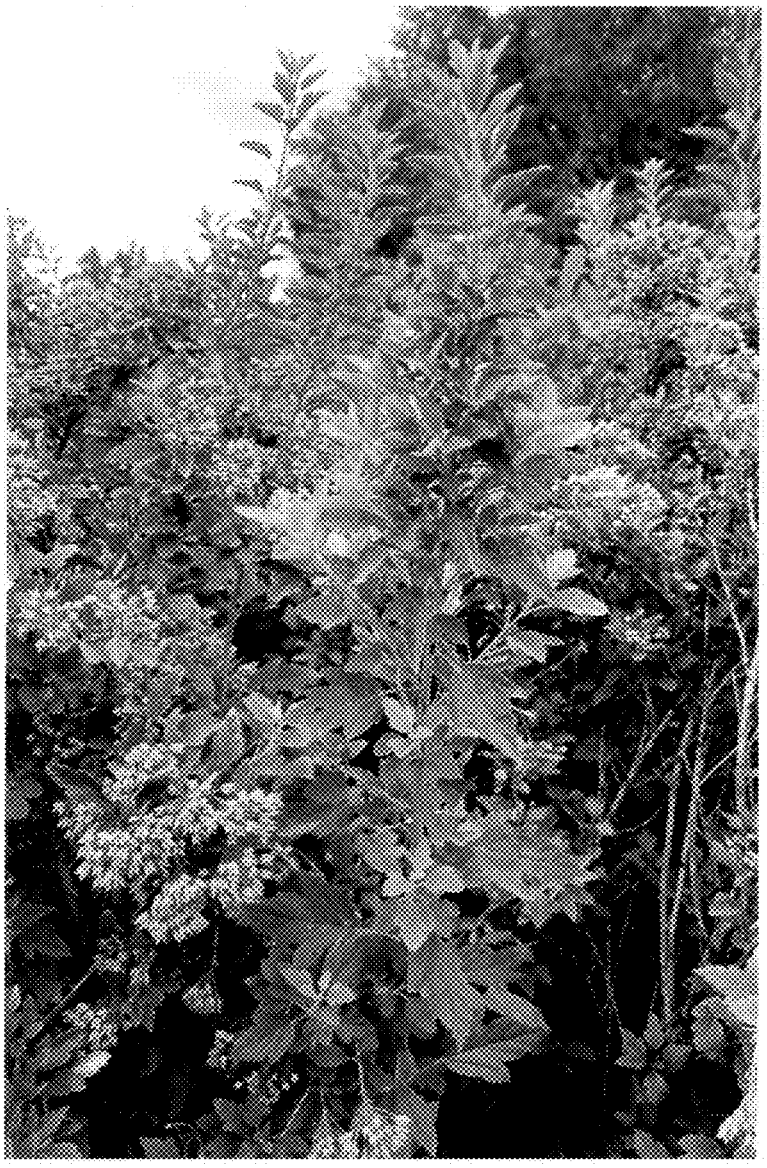
FIG. 7 illustrates natural branching from axillary buds on a current-season stem without pruning in early August and decreasing internode length as the season progresses.
Figure 8:
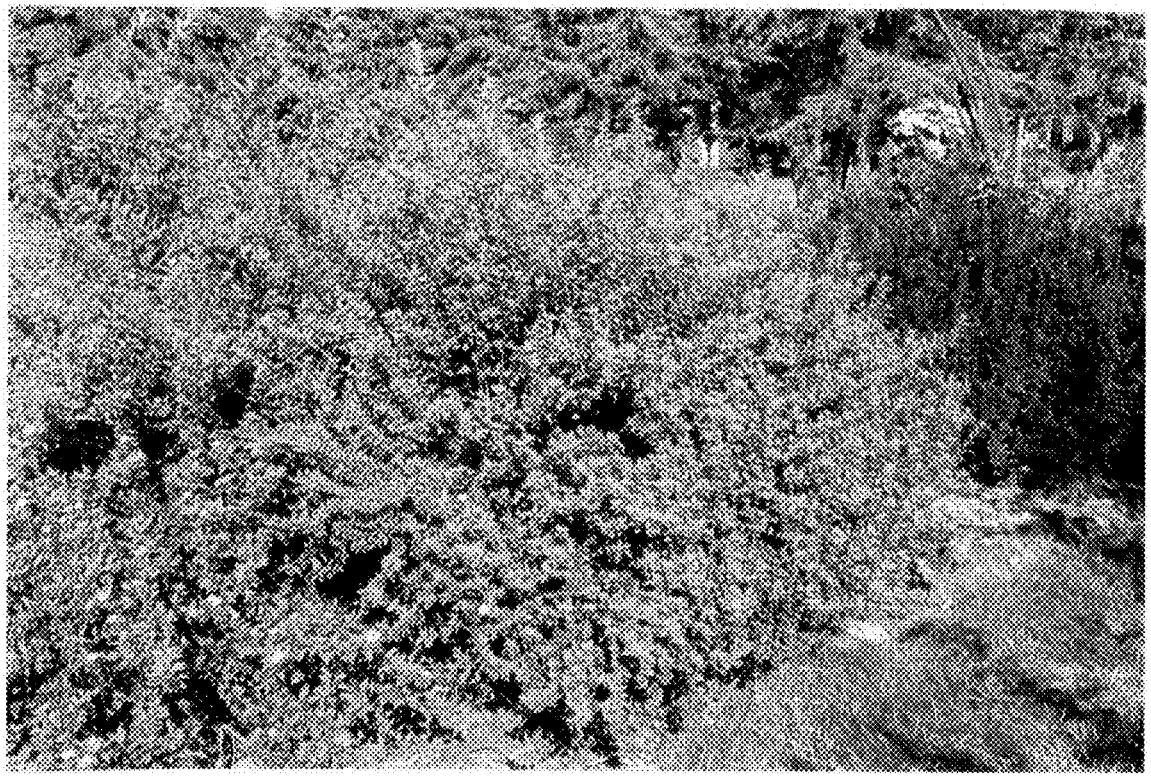
FIG. 8 illustrates the whole plant in late August with a naturally dense perimeter without pruning.
Figure 9:
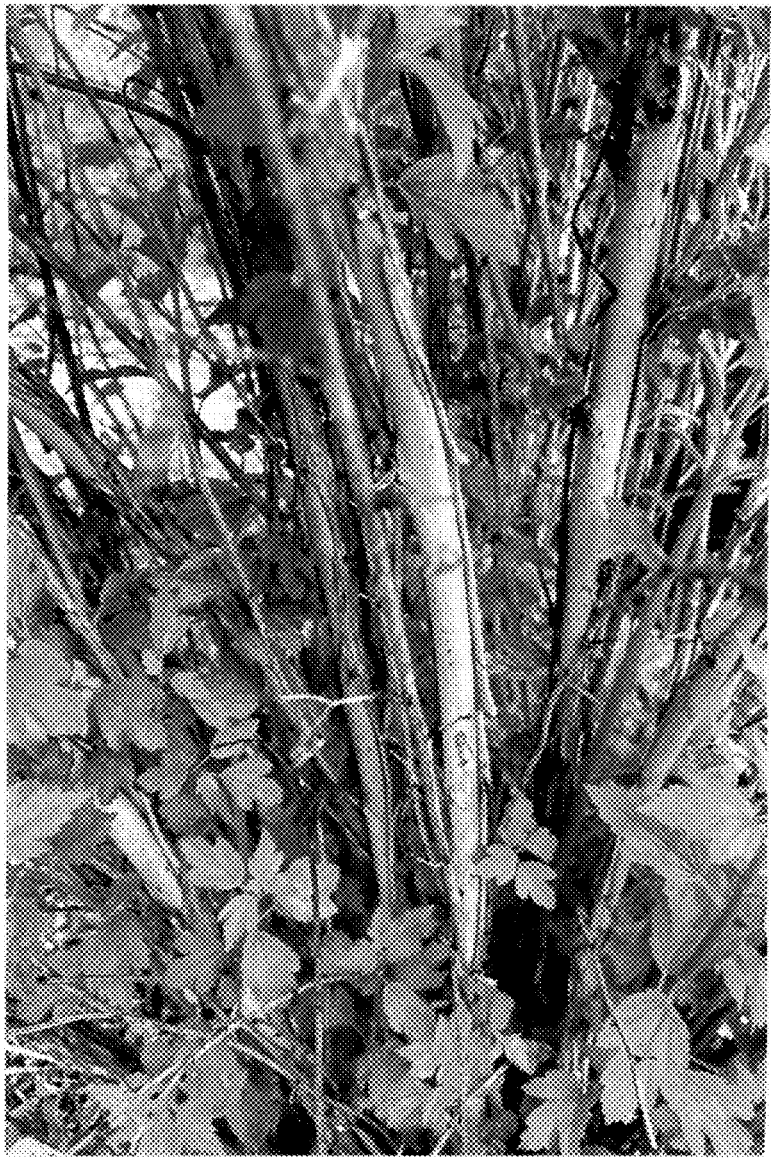
FIG. 9 illustrates exfoliating bark at the base of the plant.

The following is a detailed description of 'SueCKat', the new *Physocarpus opulifolius* cultivar, with color descriptions using terminology in accordance with The Royal Horticultural Society (London) Colour Chart (2015), except where ordinary dictionary significance of color is indicated. The phenotype of the new cultivar may vary with variations in environmental, climatic, and cultural conditions, as it has not been tested under all possible environmental conditions. Descriptions are based on observations of the ortet during its sixth growing season in 2022 in a garden bed in River Falls, Wisc.

Classification:

*Botanical.*—*Physocarpus opulifolius* 'SueCKat'.

*Common names of the species.*—Ninebark, common ninebark, Atlantic ninebark, and Eastern ninebark.

*Commercial.*—Deciduous shrub.

Parentage:

*Origin.*—Seedling of 'ZLEBic5' as the maternal parent and a full sibling of 'ZLEBic5' as the male parent.

General description:

*Plant habit.*—Upright, mounded, and compact.

*Plant size.*—1.0-1.3 m in overall height and width.

*Growth habit.*—Vigorous and dense with abundant branching.

*Blooming period.*—About 21 days from early to late June.

*Hardiness.*—Cold hardy to at least USDA Zone 4.

*Root description.*—Fibrous and vigorous.

*Diseases and pest resistance.*—'SueCKat' has shown well above average resistance to powdery mildew with other ninebark genotypes heavily infected with powdery mildew growing adjacent to it. There are multiple species of fungi that cause powdery mildew on ninebark (*Phyllactinia guttata, Podosphaera aphanis* var. *physocarpi*, and *Podosphaera macularis*), and it is unclear which species were infecting it and the adjacent, much more susceptible ninebark genotypes.

*Cultural requirements.*—'SueCKat' does well in full to partial, sun and well-drained, moderately fertile soil.

Growth and propagation:

*Propagation.*—Softwood and semi-hardwood stem cuttings have been effective.

*Time required for root initiation and initial development.*—It takes about 3 to 4 weeks during the summer using intermittent mist in a greenhouse without supplemental lighting for cuttings to typically form visible roots.

*Time required to obtain a well-rooted cutting.*—It takes about 6 to 7 weeks to produce a well-rooted cutting in a 2-inch diameter and deep container.

Branch description:

*Branch color.*—The color of current season stems is Yellow-Green Group N144C. Sides of current season's stems in full sun had reddish highlights closest to Red-Purple Group 58A. The most mature stems on four-year-old plants had a mixture of colors on the exfoliating bark; primarily Greyed-Orange Group 164A and Greyed-Orange Group 164C, but there were also lighter colored areas close to Greyed-Yellow Group 161D and darker colored areas close to Greyed-Orange 166A.

*Branch size.*—Branches produced during the current season of growth ranged from approximately 12-60 cm in length and 1-4 mm in width. The oldest branches on a six-year-old plant were up to 1.5 cm in diameter at the base of the plant.

*Branch surface.*—Young stems: Glabrous with a slight sheen. Older stems: Exfoliating bark layers that are somewhat dull and no longer have a sheen.

*Internode length.*—0.3-2.0 cm. There is a trend for internode length to decrease as the growing season progresses.

*Branch habit.*—Vigorous current season's stems tend to produce new stems from axillary buds without pruning. This leads to an abundantly branched and dense plant. The angle between the new stems arising from axillary buds and the stem from which they originated is typically 20-60°.

Foliage description:

*Overall leaf size.*—Leaf length is 4.5-7.0 cm and leaf width is 2.5-3.5 cm.

*Leaf division.*—Simple.

*Leaf attachment.*—Petiolate.

*Leaf arrangement.*—Alternate.

*Leaf number.*—It varies, but a vigorous growing branch typically produces 30-60 leaves in a growing season.

*Leaf blade shape.*—Ovate in overall outline with three prominent lobes.

*Leaf blade base.*—Rounded to slightly cordate.

*Leaf blade apex.*—Acute to cuneate.

*Leaf blade venation.*—Primary venation is palmate with three principal veins. The principal veins diverge at the juncture of the leaf blade and petiole and continue with one principal vein through the middle of each of the three lobes. Secondary venation off the three principal veins is pinnate.

*Leaf blade margin.*—The three primary lobes have secondary lobes or serrations. The margin on the three primary lobes is best described as doubly serrate. The serrations extend out from the edge of the main leaf blade about 1.0-1.5 mm and there is typically between 3-5 mm between the tips of primary serrations and 1-2 mm between the tips of secondary serrations.

*Leaf blade surface.*—Glabrous on upper and lower surfaces.

*Leaf blade size.*—The leaf blade is approximately 3.0-5.0 cm long and 2.0-3.5 cm wide.

*Leaf blade color.*—Young emerging leaf blades are between Yellow-Green Group 150A and Yellow-Green Group N144B on the upper and lower surfaces. Young expanded leaf blades are between Yellow-Green Group 144B and Yellow-Green Group 145A on the upper surface and are Yellow-Green Group 144B on the lower surface. Mature leaves are Green Group 137B on the upper surface and Green Group 137C on the lower surface. Where the sun especially hits the upper surface of the leaves, the color can be Yellow-Green Group N144A.

*Petiole size.*—1.0-2.5 cm in length and about 1.0 mm in width.

*Petiole shape.*—Sulcate. The petiole is generally round except for a longitudinal furrow running the length of the upper surface.

*Petiole color.*—Yellow-Green Group 144B.

*Petiole texture.*—Glabrous.

*Stipule number.*—There are two stipules at each node with one on each side of the leaf petiole.

*Stipule size.*—2.0-3.0 mm long and 1.25 mm wide.

*Stipule shape.*—Generally lanceolate.

*Stipule color.*—Yellow-Green Group 144B on the upper and lower surfaces.

Flower description:

*Inflorescence type.*—A corymb with 18-27 rotate flowers arranged in a hemisphere.

*Inflorescence size.*—Typically 1.5-2.0 cm in height and width.

*Inflorescence lastingness.*—The corymb has open flowers typically for up to 21 days with each individual flower open for approximately 3 days.

*Flower bud shape.*—Oval to spherical.

*Flower bud size and proportions.*—2.0-2.25 mm in length and 2.0 mm in width. The receptacle of the bud accounts for about half of the proximal end and the calyx accounts for about half of the distal end of an unopened flower bud.

*Flower bud color.*—The overall color of exposed petal undersides as the sepals open can best be described as White Group N155C. The sepals are Yellow-Green Group 144C and the receptacle color is Yellow-Green Group 153C.

*Flower size when fully open.*—5.0 mm in diameter and 3.0-4.0 mm in depth (not including pedicel).

*Flower symmetry.*—Actinomorphic.

*Flower fragrance.*—Slight and sweet.

*Petal number.*—5.

*Petal size.*—2.0 mm in length and 1.5 mm in width.

*Petal shape.*—Elliptic to obovate.

*Petal color.*—Expanding petals are White Group 155C on the upper and lower surfaces.

*Sepal number.*—5.

*Sepal size.*—Length is 1.5-2.0 min and width is 1.0-1.25 mm.

*Sepal shape.*—Deltoid.

*Sepal color.*—Yellow-Green Group N144D on the adaxial side and Yellow-Green Group 146D on the abaxial side.

*Sepal texture.*—Hoary on both surfaces.

*Pedicel size.*—The length ranges from about 1.25 cm for the flowers coming from the proximal or lower end of the corymb to about 0.5 cm for the flowers nearest the terminal or center of the corymb. Pedicels are round in cross section and about 0.25-0.75 mm in diameter.

*Pedicel color.*—Yellow-Green Group 144C.

*Pedicel and receptacle texture.*—Glabrous.

*Subtending bract size.*—There is a subtending bract where each pedicel meets the peduncle of the corymb. The subtending bract is 1.0-2.0 mm long and 1.0 mm wide below where the pedicels attach at the proximal end of the corymb to 1.0-1.5 mm long and 0.75-1.0 mm wide under the more distal pedicels at the terminal or top of the corymb.

*Subtending bract shape*.—Elliptic to obovate with 3-5 very small and irregularly spaced serrations.

*Subtending bract color*.—Yellow-Green Group 144C on both sides.

Gynoecium:

*Pistil number per flower*.—Typically there are 4, but sometimes 3.

*Stigma shape*.—Globular.

*Stigma size*.—0.25 mm in height and width.

*Stigma color*.—Yellow Green Group 144D.

*Style shape*.—Linear

*Style size*.—About 2.0 mm long and 0.2 mm wide.

*Style color*.—Green-White Group 157C.

*Ovary shape*.—Elliptic.

*Ovary size*.—About 0.4 mm in length and 0.2 mm in width.

*Ovary color*.—Yellow Green Group 144C.

Androecium:

*Stamen number per flower*.—Approximately 25.

*Anther shape*.—Elliptic to round.

*Anther size*.—0.3 mm in height and width.

*Anther color*.—Purple Group N77D upon flowers opening and darkening to Purple Group N77A after dehiscence.

*Pollen color*.—White Group 155C.

*Pollen abundance*.—Moderate.

*Filament shape*.—Linear.

*Filament size*.—1.0-2.0 mm long and 0.1-0.2 mm wide.

*Filament color*.—Green White Group 157C.

Fruit and seeds:

*Fruit*.—There are typically three or four firm-walled follicles that form per flower. Follicles can split along both sides of the seam, but split more readily along the inner or adaxial seam. Follicles are elongated and generally ovate in shape with acuminate tips. They are up to 6.0 mm long and approximately 2.0 mm wide at their widest point. After fertilization and expansion of successfully developing fruit, the follicle surface has a pastel coral pink color in bright light close to Orange-Red Group 37C. Follicle color tends to be green when out of direct sunlight and near Yellow-Green Group 145C. As the follicles continue to mature the coral-pink coloration dissipates. When mature and before drying out and turning brown, the color is Greyed-Yellow Group 161A. The final color when follicles are dry and open to release seeds is Greyed-Orange Group 165A.

*Seeds per follicle*.—There are typically 1-2 seeds per follicle.

*Seed shape*.—Ovate.

*Seed size*.—Up to about 1.5 mm long and 1.25 mm wide.

*Seed color*.—Mature seed color as follicles open and seeds dehisce is closest to Greyed-Orange Group 164B.

Winter hardiness: Acclimated plants of 'SueCKat' have displayed strong stem survival (complete survival to minor tip dieback) in United States Department of Agriculture cold hardiness zone 4 without insulation.

I claim:

1. A new and distinct cultivar of *Physocarpus opulifolius* plant named 'SueCKat' substantially as herein shown and described, characterized particularly by its upright, mounded, dense plant habit; compact overall plant size; strong branching characteristics; small yellow-green foliage; short internode length that becomes shorter as the growing season progresses; resistance to powdery mildew; corymbs of small white flowers; green follicle color with very light coral-pink highlights in full sun for about a month after fertilization; and ability to root and grow vigorously from softwood and semi-hardwood stem cuttings.

* * * * *